US008430806B2

(12) United States Patent
Ni et al.

(10) Patent No.: US 8,430,806 B2
(45) Date of Patent: Apr. 30, 2013

(54) ELECTRONIC DEVICE AND HYPNOSIS METHOD UTILIZING THE SAME

(75) Inventors: Yuan Ni, Shenzhen (CN); Hong-Yan Yu, Shenzhen (CN)

(73) Assignees: Shenzhen Futaihong Precision Industry Co., Ltd., Shenzhen (CN); Chi Mei Communication Systems, Inc., New Taipei (TW)

( * ) Notice: Subject to any disclaimer, the term of this patent is extended or adjusted under 35 U.S.C. 154(b) by 276 days.

(21) Appl. No.: 12/797,491

(22) Filed: Jun. 9, 2010

(65) Prior Publication Data

US 2011/0160524 A1 Jun. 30, 2011

(30) Foreign Application Priority Data

Dec. 30, 2009 (CN) .......................... 2009 1 0312825

(51) Int. Cl.
*A61M 21/02* (2006.01)

(52) U.S. Cl.
USPC ........................................................... 600/28

(58) Field of Classification Search .............. 600/26–28, 600/508–513, 544, 545, 547; 128/897–899
See application file for complete search history.

(56) References Cited

U.S. PATENT DOCUMENTS 6,897,788 B2 * 5/2005 Khair et al. .............. 340/870.16
2010/0010289 A1 * 1/2010 Clare ............................. 600/27

FOREIGN PATENT DOCUMENTS

CN 101584903 A 11/2009

* cited by examiner

*Primary Examiner* — Christine Matthews
*Assistant Examiner* — Joshua D Lannu
(74) *Attorney, Agent, or Firm* — Altis Law Group, Inc.

(57) ABSTRACT

An electronic device and hypnosis method includes setting a hypnosis volume level and a playing duration of the electronic device. An audio file is played in response to the electronic device being activated, and a brain wave frequency of a user is determined. The electronic device and hypnosis method further includes analyzing the brain wave frequency to determine if the user is in a sleeping state, and playing the audio file for the playing duration at the hypnosis volume level.

10 Claims, 3 Drawing Sheets

ELECTRONIC DEVICE AND HYPNOSIS METHOD UTILIZING THE SAME

BACKGROUND

1. Technical Field

Embodiments of the present disclosure relate to hypnosis technology, and more particularly to an electronic device and hypnosis method for utilizing the electronic device.

2. Description of Related Art

Insomnia due to depression, anxiety, stress, or other types of stress may be relieved by hypnosis for some people. However, the hypnosis may cause side effects. How to have a good sleep without taking any medicine is important for people.

What is needed, therefore, is an improved electronic device and hypnosis method using the electronic device.

DETAILED DESCRIPTION

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

In general, the word "module," as used herein, refers to logic embodied in hardware or firmware, or to a collection of software instructions, written in a programming language, such as, for example, Java, C, or Assembly. One or more software instructions in the modules may be embedded in firmware, such as an EPROM. It will be appreciated that modules may comprised connected logic units, such as gates and flip-flops, and may comprise programmable units, such as programmable gate arrays or processors. The modules described herein may be implemented as either software and/or hardware modules and may be stored in any type of computer-readable medium or other computer storage system.

Figure 1:
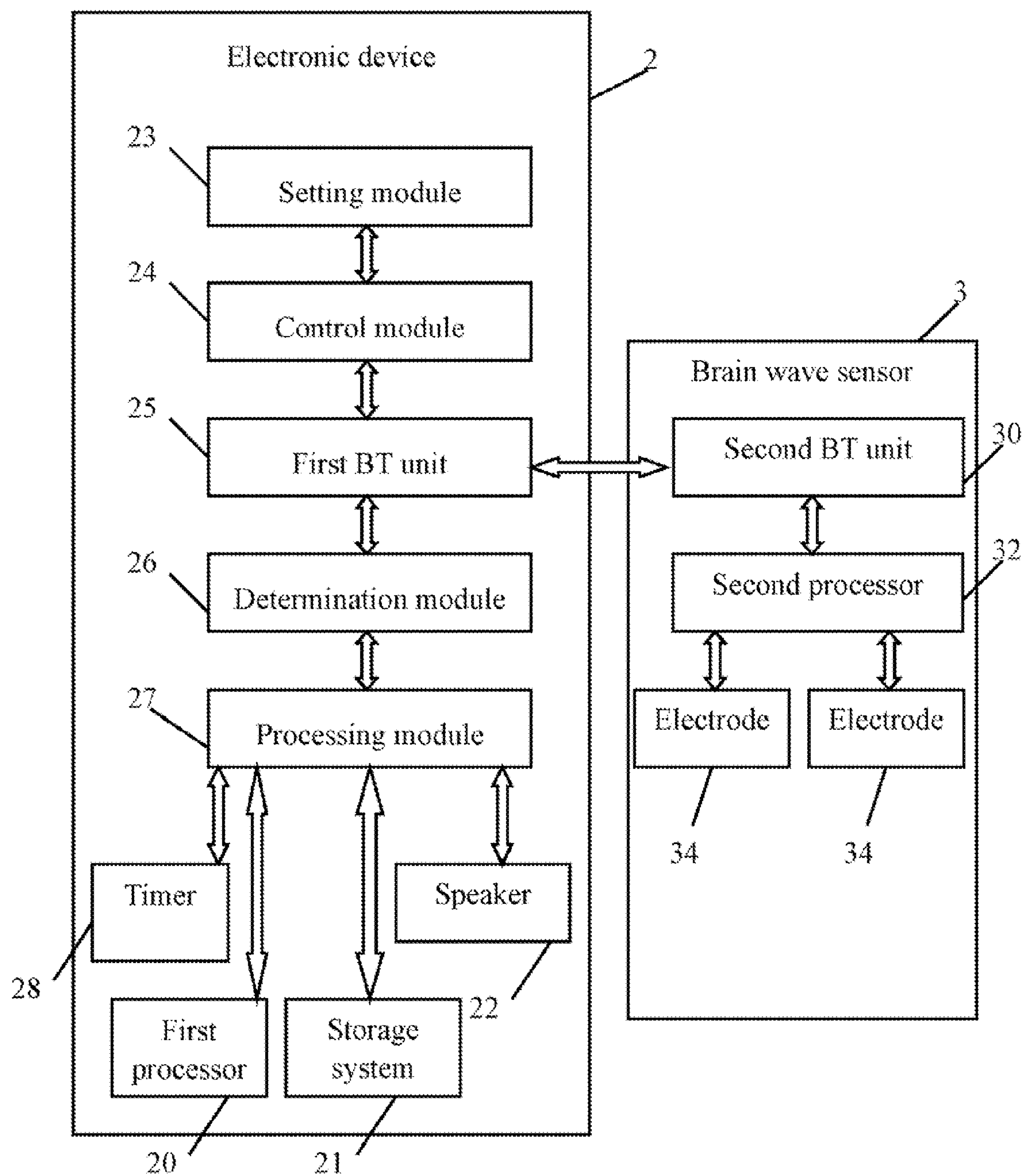
FIG. 1 is a block diagram of some embodiments of an electronic device in communication with a brain wave sensor.

FIG. 1 is a block diagram of some embodiments of an electronic device 2 in communication with a brain wave sensor 3. In some embodiments, the electronic device 2 determines a brain wave frequency of a user using the brain wave sensor 3, and plays audio files at a predetermined volume for a predetermined duration to help the user fall asleep. The electronic device 2 includes a first BLUETOOTH (BT) unit 25, and the brain wave sensor 3 includes a second BT unit 30. The electronic device 2 establishes a communication with the brain wave sensor 3 through the first BT unit 25 and the second BT unit 30, and acquires brain wave signals of the user from the brain wave sensor 3 through the communication.

In some embodiments, the brain wave sensor 3 may be embedded in a cap/hat, or a headset, for example. The brain wave sensor 3 also includes a second processor 32, and one or more electrodes 34. The second processor 32 may execute one or more computerized operations of the brain wave sensor 3. Detailed operations of the one or more electrodes 34 are provided below.

The electronic device 2 may be a mobile phone, a personal digital assistant, or any other kind of computing device. The electronic device 2 also includes a first processor 20, a storage system 21, a speaker 22, and a timer 28. The first processor 20 executes one or more computerized operations of the electronic device 2 and other applications, to provide the functions of the electronic device 2. The storage system 21 stores one or more programs, such as programs of the operating system, other applications of the electronic device 2, and various kinds of data, such as messages, E-mails, or audio files, for example. In some embodiments, the electronic device 2 may be a mobile phone, and the storage system 21 may be a memory of the electronic device 2 or an external storage card, such as a memory stick, a smart media card, a compact flash card, or any other type of memory card. The speaker 22 may output audible data, such as music, rings, for example. The timer 28 may time a predetermined duration. Detailed information will be provided below.

In some embodiments, the electronic device 2 further includes a setting module 23, a control module 24, a determination module 26, and a processing module 27. The modules 23, 24, 26, and 27 may comprise one or more computerized codes to be executed by the first processor 20 to perform one or more operations of the electronic device 2. Details of these operations are provided below.

The setting module 23 defines a frequency band of brain waves of the user to determine if the user is in a sleeping state. In some embodiments, the defined frequency band may be in a range of 8 Hz to 12 Hz. Brain wave frequencies of people may change in accordance with different states of people. For example, a frequency of alpha waves of the brain waves may be in the range of 8 Hz to 12 Hz before people falls asleep, and may change to be in a range of from 12 Hz to 14 Hz once falling asleep.

The setting module 23 also sets a hypnosis volume level and a playing duration of the electronic device 2. The hypnosis volume level may be a volume level that helps people to fall asleep easier. For example, the hypnosis volume level can be 40 decibels (dB). The playing duration may be preset according to user requirements, such as 20 minutes, for example.

The setting module 23 may further set a switch-on command and a switch-off command of the electronic device 2, to control the electronic device 2 and the one or more electrodes 34. The switch-on command and the switch-off command may be hotkeys of a keyboard of the electronic device 2, or character strings. For example, the user may press the hotkeys or input the character strings to invoke the switch-on command or the switch-off command. In some embodiments, the switch-on command may be sent to the second processor 32 to enable the one or more electrodes 34, and the switch-off command may be sent to the second processor 32 to disable the one or more electrodes 34.

In response that the switch-on command is invoked, the process module 27 starts to play an audio file using the speaker 22, and the control module 24 controls the one or more electrodes 34 to collect brain wave signals of the user by sending the switch-on command to the brain wave sensor 3. In some embodiments, the audio file may be predetermined by the user. For example, the audio file may be a specific kind of music, such as soft/quiet music. The second BT unit 30 sends the brain wave signals to the first BT unit 25.

The determination module 26 determines a brain wave frequency according to the brain wave signals of the user. In some embodiments, the brain wave signals are analog signals, the determination module 26 converts the brain wave signals to digital signals, and determines the brain wave frequency according to the digital signals.

The determination module 26 further analyzes the brain wave frequency according to the defined frequency band, to determine if the user is in the sleeping state.

In some embodiments, the determination module 26 determines if the brain wave frequency is within the defined frequency band. If the brain wave frequency is within the defined frequency band, the determination module 26 determines that the user is in the sleeping state. If the brain wave frequency is not within the defined frequency band, the determination module 26 determines that the user is not in the sleeping state.

For example, if the brain wave frequency is 6 Hz, the determination module 26 determines that the user is not in the sleeping state as 6 Hz does not fall in the range of 8 Hz to 12 Hz.

If the user is in the sleeping state, the processing module 27 plays the audio file at the hypnosis volume level, and enable the timer 28 to start timing the playing duration. In some embodiments, the audio file is played with a volume of 80 dB firstly, which may be changed to the hypnosis volume level (e.g., 40 dB) in response to determining the user is in the sleeping state. When the timer 28 determines that the playing duration elapses, the switch-off command is invoked. According to the switch-off command, the processing module 27 stops playing the audio file, and the control module 24 sends the switch-off command to the second processor 30 through the communication. The switch-off command is used to stop the one or more electrodes 34 from collecting the brain wave signals of the user.

Playing the audio file at the hypnosis volume level during the playing duration not only helps the user to fall asleep easier, but also avoids awakening the user if the audio file is stopped suddenly. Further, the control module 24 stops the one or more electrodes 34 from operating to conserve power of the electronic device 2.

Figure 2:
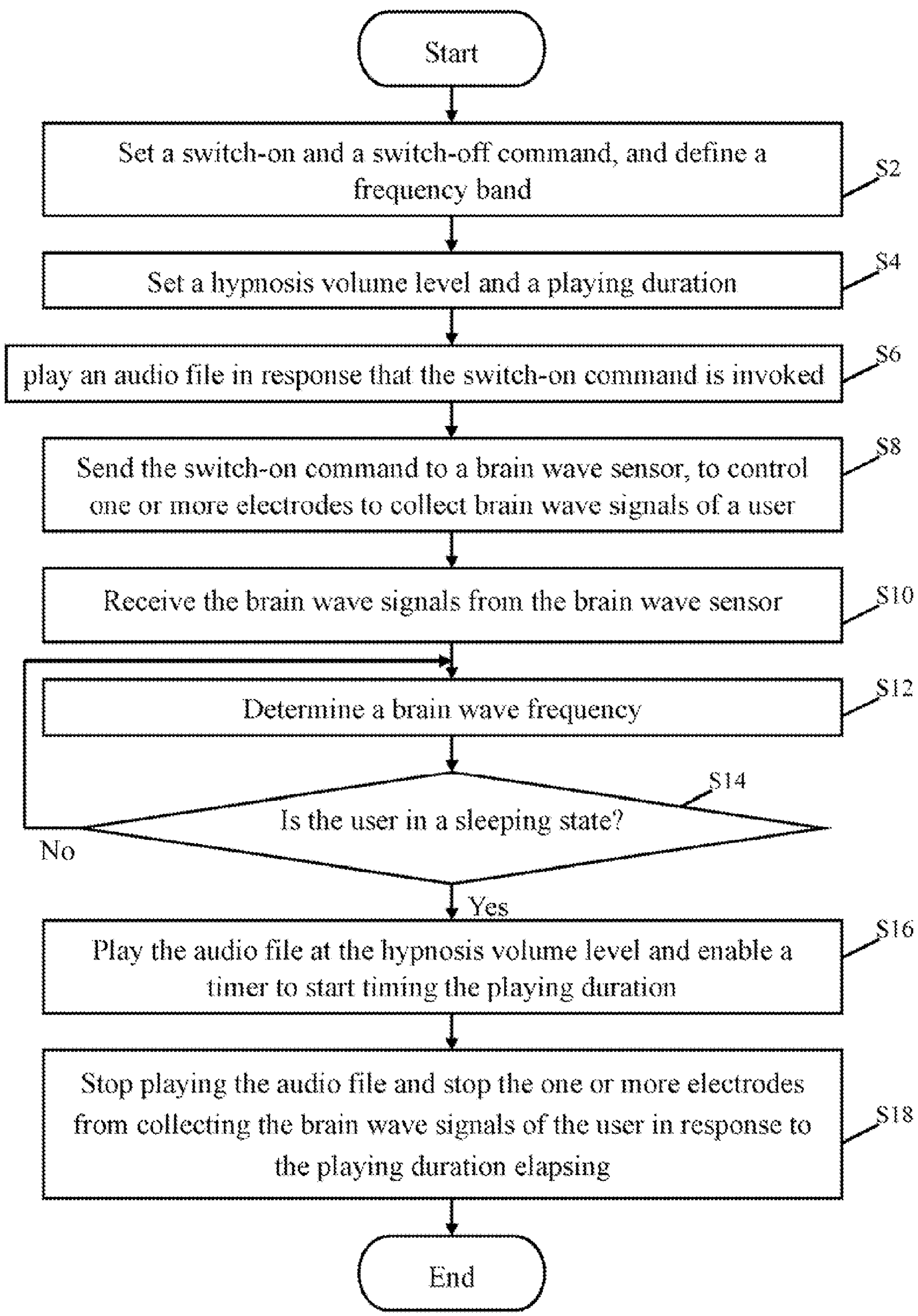
FIG. 2 is a flowchart of some embodiments of a hypnosis method using the electronic device of FIG. 1.

FIG. 2 is a flowchart of some embodiments of a hypnosis method using the electronic device 2 of FIG. 1. Depending on the embodiment, additional blocks may be added, others removed, and the ordering of the blocks may be replaced.

In block S2, the setting module 23 defines a frequency band of brain waves of a user to determine if the user is in a sleeping state, and sets a switch-on command and a switch-off command to control the electronic device 2 and the one or more electrodes 34. As mentioned above, the defined frequency band may be in a range of 8 Hz to 12 Hz.

In block S4, the setting module 23 also sets a hypnosis volume level and a playing duration of the electronic device 2.

In response that the switch-on command is invoked, in block S6, the process module 27 starts to play an audio file.

In block S8, the control module 24 sends the switch-on command to the second processor 32 of the brain wave sensor 3, to control the one or more electrodes 34 to collect brain wave signals of the user. Then the brain wave sensor 3 sends the brain wave signals of the user to the electronic device 2 through the second BT unit 30.

In block S10, the electronic device 2 receives the brain wave signals from the brain wave sensor 3 through the first BT unit 25.

In block S12, the determination module 26 determines a brain wave frequency according to the brain wave signals of the user.

In block S14, the determination module 26 analyzes the brain wave frequency according to the defined frequency band, to determine if the user is in the sleeping state. Detailed descriptions are provided in FIG. 3.

If the user is not in the sleeping state, the procedure returns to block S12, the first BT unit 25 continues to receive the brain wave signals from the brain wave sensor 3.

If the user is in the sleeping state, in block S16, the processing module 27 plays the audio file at the hypnosis volume level, and enable the timer 28 to start timing the playing duration.

In response to the timer 28 determining that the playing duration elapses, in block S18, the processing module 27 stops playing the audio file, and the control module 24 sends the switch-off command to the second processor 30, to stop the one or more electrodes 34 from collecting the brain wave signals of the user.

Figure 3:
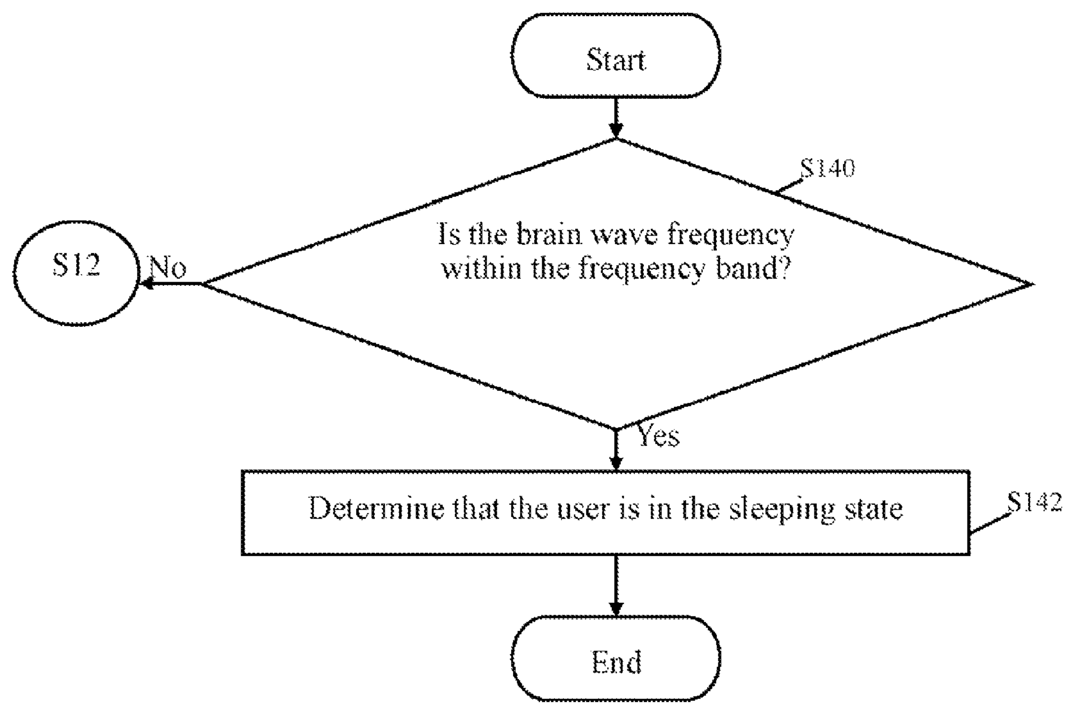
FIG. 3 is a flowchart of detailed descriptions of block S14 in FIG. 3.

FIG. 3 is a flowchart of detailed descriptions of S14 in FIG. 3. Depending on the embodiment, additional blocks may be added, others removed, and the ordering of the blocks may be replaced.

In block S140, the determination module 26 determines if the brain wave frequency is within the defined frequency band. If the brain wave frequency is not within the defined frequency band, the procedure returns to block S12.

If the brain wave frequency is within the defined frequency band, in block S142, the determination module 26 determines that the user is in the sleeping state.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. A hypnosis method using an electronic device, the method comprising:

defining a frequency band of brain waves of a user to determine whether the user is in a sleeping state;

setting a switch-off command of the electronic device;

setting a hypnosis volume level and a playing duration of the electronic device;

playing an audio file at an original volume level in response to the electronic device being activated;

determining a brain wave frequency according to brain wave signals of the user collected by a brain wave sensor;

analyzing the brain wave frequency according to the defined frequency band, to determine whether the user is in the sleeping state;

playing the audio file at the hypnosis volume level and enabling a timer of the electronic device to start timing the playing duration when the user is in the sleeping state; and in response to the playing duration elapsing, stopping playing the audio file, and sending the switch-off command to the brain wave sensor to stop collecting the brain wave signals of the user.

2. The method according to claim 1, wherein the analyzing step comprises:

determining that the user is in the sleeping state when the brain wave frequency is within the defined frequency band.

3. The method according to claim 1, wherein the collecting step comprises:

collecting the brain wave signals of the user by one or more electrodes of the brain wave sensor; and sending the brain wave signals to the electronic device.

4. The method according to claim 1, further comprising:

setting a switch-on command of the electronic device.

5. The method according to claim 4, further comprising:

sending the switch-on command to the brain wave sensor to start collecting the brain wave signals of the user.

6. A non-transitory computer readable storage medium storing a set of instructions, the set of instructions capable of being executed by a processor to perform a hypnosis method using an electronic device, the method comprising:

defining a frequency band of brain waves of a user to determine whether the user is in a sleeping state;

setting a switch-off command of the electronic device;

setting a hypnosis volume level and a playing duration of the electronic device;

playing an audio file at an original volume level in response to the electronic device being activated;

determining a brain wave frequency according to brain wave signals of the user collected by a brain wave sensor;

analyzing the brain wave frequency according to the defined frequency band, to determine whether the user is in the sleeping state;

playing the audio file at the hypnosis volume level and enabling a timer of the electronic device to start timing the playing duration when the user is in the sleeping state; and in response to the playing duration elapsing, stopping playing the audio file, and sending the switch-off command to the brain wave sensor to stop collecting the brain wave signals of the user.

7. The storage medium as claimed in claim 6, wherein the analyzing step comprises:

determining that the user is in the sleeping state when the brain wave frequency is within the defined frequency band.

8. The storage medium as claimed in claim 6, wherein the collecting step comprises:

collecting the brain wave signals of the user by one or more electrodes of the brain wave sensor; and sending the brain wave signals to the electronic device.

9. The storage medium as claimed in claim 6, wherein the method further comprises:

setting a switch-on command of the electronic device.

10. The storage medium according to claim 9, wherein the method further comprises:

sending the switch-on command to the brain wave sensor to start collecting the brain wave signals of the user.

* * * * *